(12) United States Patent
Kladders et al.

(10) Patent No.: US 8,001,965 B2
(45) Date of Patent: *Aug. 23, 2011

(54) CAPSULE FOR TAKING AN ACTIVE SUBSTANCE WHICH CAN BE INHALED

(75) Inventors: Heinrich Kladders, Muelheim (DE); Burkhard Metzger, Ingelheim (DE); Dieter Hochrainer, Schmallenberg (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 226 days.

This patent is subject to a terminal disclaimer.

(21) Appl. No.: 12/365,563

(22) Filed: Feb. 4, 2009

(65) Prior Publication Data

US 2009/0181191 A1    Jul. 16, 2009

Related U.S. Application Data

(63) Continuation of application No. 10/757,047, filed on Jan. 14, 2004.

(60) Provisional application No. 60/449,972, filed on Feb. 25, 2003.

(30) Foreign Application Priority Data

Jan. 14, 2003 (DE) .................................. 103 00 984

(51) Int. Cl.
*A61M 11/00* (2006.01)
(52) U.S. Cl. .......... 128/203.12; 128/203.15; 128/203.21
(58) Field of Classification Search ............. 128/203.15, 128/203.21; 604/58
See application file for complete search history.

(56) References Cited

U.S. PATENT DOCUMENTS

| 4,889,114 A | 12/1989 | Kladders |
|---|---|---|
| 5,152,284 A | 10/1992 | Valentini |
| 5,715,811 A | 2/1998 | Ohki et al. |
| 5,947,118 A | 9/1999 | Hochrainer |
| 6,585,294 B1 | 7/2003 | Faulstroh |
| 2001/0008637 A1 | 7/2001 | Hochrainer et al. |
| 2003/0108705 A1 | 6/2003 | Duffield et al. |
| 2004/0131668 A1 | 7/2004 | Hochrainer et al. |

FOREIGN PATENT DOCUMENTS

| DE | 3345722 A1 | 6/1985 |
|---|---|---|
| DE | 3927170 A1 | 2/1991 |
| DE | 19835346 A1 | 2/2000 |
| EP | 0143524 A1 | 6/1985 |
| EP | 0911047 A1 | 4/1999 |
| EP | 1100474 B1 | 7/2002 |
| GB | 2356842 A | 6/2001 |
| WO | 9102558 | 3/1991 |
| WO | 00/07572 A2 | 2/2000 |

OTHER PUBLICATIONS

Abstract for DE 3345722: WPIDS 1985-160068, (Jun. 1985).
Abstract for EP 1100474: CA 132-141964, (Jul. 2002).
Abstract for EP 911047: WPIDS 1995-014986, (Apr. 1999).

(Continued)

*Primary Examiner* — Steven O Douglas
(74) *Attorney, Agent, or Firm* — Michael P. Morris; Wendy A. Petka

(57) ABSTRACT

The invention relates to a novel capsule for receiving an active substance to be administered by inhalation, which is preferably intended for use in a powder inhaler operating on the Bernoulli principle.

9 Claims, 14 Drawing Sheets

OTHER PUBLICATIONS

Office Action for co-pending U.S. Appl. No. 10/757,047, dated Apr. 17, 2007.
Office Action for co-pending U.S. Appl. No. 10/757,047, dated Oct. 4, 2007.
Office Action for co-pending U.S. Appl. No. 10/757,047, dated Dec. 11, 2007.
Office Action for co-pending U.S. Appl. No. 10/757,047, dated Feb. 22, 2008.
Office Action for co-pending U.S. Appl. No. 10/757,047, dated May 7, 2009.

38

39

40

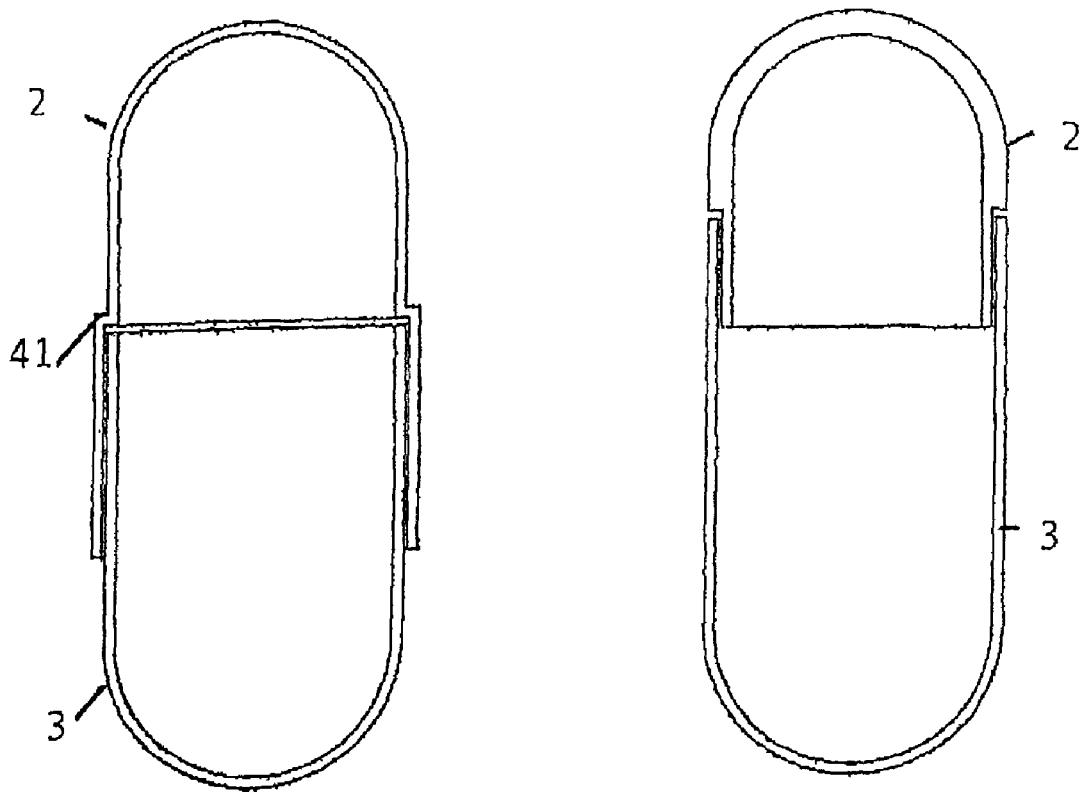

CAPSULE FOR TAKING AN ACTIVE SUBSTANCE WHICH CAN BE INHALED

CROSS REFERENCE TO RELATED APPLICATIONS

This Application is a continuation application of U.S. patent application Ser. No. 10/757,047, filed Jan. 14, 2004, which claims the benefit of U.S. Provisional Patent Application No. 60/449,972, filed Feb. 25, 2003, the entire disclosures of which are hereby incorporated by reference.

BACKGROUND

The invention relates to a novel capsule for receiving an active substance to be administered by inhalation, which is preferably intended for use in a powder inhaler operating on the Bernoulli principle.

A number of powder inhalers operating by various principles are known in the literature. What they all have in common is that the active substance to be delivered is stored in a generally cylindrical capsule and this capsule is inserted in a capsule chamber of the inhaler.

A suitable powder inhaler consists essentially of a preferably cylindrical capsule chamber provided with means for laterally opening the capsule, an air inlet opening in the capsule chamber and an air outlet opening and a mouthpiece provided downstream of the air outlet opening. The capsule chamber is usually cylindrical in shape, being somewhat longer and wider than the capsule so that the capsule is able to vibrate both axially and radially therein, but remains aligned substantially parallel to the chamber axis. The terms axial and radial are equivalent to vertical (axial) and horizontal (radial) with respect to the orientation of the inhaler in which the capsule chamber is aligned below the mouthpiece. Axial also denotes an orientation parallel to the longitudinal axis of the inhaler (vertical axis), while radial is the direction perpendicular thereto. The capsule chamber has an air inlet in the region of one of its two ends and an air outlet opening in the region of its other end. The air outlet which can carry a powder aerosol leads to a mouthpiece. In order to deliver the active capsule contents, first of all the capsule may be opened, normally at two places on its longitudinal casing. As a rule the openings are located close to the two longitudinal ends of the capsule. If an air stream is now generated from the air inlet towards the air outlet in the capsule chamber, it runs along the longitudinal axis of the capsule and has two effects: on the one hand the capsule is moved mainly along its longitudinal axis by the air stream. It can also vibrate to a small degree. On the other hand, the air flowing along the two capsule openings produces a lower pressure in front of the capsule openings than inside the capsule, so that the powder contained in the capsule is picked up by the air stream and thereby nebulised.

DE 3345722 discloses an inhaler of this kind consisting of two housing elements which are axially moveable towards each other, with a single capsule chamber.

WO 91/02558 discloses another inhaler as described hereinbefore wherein instead of a single capsule chamber there are a plurality of capsule chambers arranged in a similar manner to a revolver magazine. The open ends of this magazine are delimited by walls, the air inlet or air outlet being located only at one point in these walls. This magazine is mounted to be rotatable so that a capsule chamber is only connected to the air inlet, the air outlet and the cutting elements required to open the capsule in a certain position.

EP 0911047 discloses an inhaler with a) a cup-shaped lower part open upwardly, b) a plate which covers the opening in the lower part and perpendicular to which is formed a capsule chamber, whilst on the capsule chamber is provided a button which is moveable against a spring which has two sharp spikes for opening the capsule, c) an upper part with a mouth tube which is connected to the capsule chamber, and capable of conveying a powder aerosol, and d) a lid. The elements a), b), c) and d) are joined together by a common hinge element so that they can be flipped relative to each other. In addition, this patent application describes a capsule holder wherein the capsule holder may be constructed as a hole in the plate b) and has ribs at the edge. The capsule is jammed into this capsule holder to hold it in readiness.

The capsules normally used for inhalers of this kind consist of hard gelatine but may also consist of a plastic material. In connection with this reference is made to EP 1100474.

The capsules known from the prior art consist of two cup-like components which fit telescopically one inside the other, the capsule cap and the capsule body. The outer shape of a composite capsule of this kind is that of a closed cylinder with hemispherical ends. The cylinder has a longitudinal axis and a transverse axis. The longitudinal axis is the axis which runs parallel to the generatrix of the cylinder casing. The longitudinal axis is longer than the transverse axis with the result that the longitudinal section of the capsule has an oval geometry and the cross section has a circular geometry. Many capsules have an encircling groove at the join between the capsule cap and capsule body, produced by the fact that the capsule cap always has a somewhat larger external diameter than the capsule body. In connection with this, reference is made to EP 1100474 or PCT/EP0207481. If for example cross sectional drawings of the two parts of the capsule are superimposed, it will be seen that the two outer contours are not congruent.

SUMMARY OF THE INVENTION

Surprisingly, it has now been found that the capsules known from the prior art vibrate differently depending on their position of insertion in the inhaler when air flows in and the minimum air flow velocity for producing vibration of the capsule, all other things being equal, depends on whether the upper or lower part of the capsule is located in the direction of the inflow aperture. Such uncertainty is however undesirable.

Therefore, it is an aim of the present invention to provide disposable capsules as an active substance reservoir for powder inhalers, particularly powder inhalers operating by the Bernoulli effect, which behave identically irrespective of their positioning.

Another aim of the invention is to modify the known capsules so that the delivery of active substance is independent of the top-bottom orientation of the capsule in the capsule chamber.

A further aspect of the present invention relates to the use of capsules of this kind in Bernoulli powder inhalers.

The disposable capsules according to the invention have a longitudinal and a transverse axis, the longitudinal axis being longer than the transverse axis, i.e. the ratio of length of the longitudinal axis to the transverse axis, the elongation, is greater than 1. According to the invention the outer contour of the capsule is of mirror-symmetrical construction with respect to a plane of symmetry sigma H which bisects the longitudinal axis of the capsule. The longitudinal axis is positioned perpendicularly to the plane of symmetry. This mirror symmetry does not relate to the inner contour of the capsule. As a result of the symmetrical construction, the inflow and vibration conditions are identical irrespective of the direction of insertion of the capsule into the inhaler. They both show the same inflow characteristics above the air entry aperture.

Within the scope of the present invention the term "mirror symmetry" does not relate to any abstract or idealised mathematical operation but rather the transfer of this mathematical concept to what is physically and technically possible. As a result of this the term "mirror symmetry" here includes tolerances and inaccuracies resulting from the manufacturing process, for example.

By the term "inaccuracy" is meant the extent to which an element X formed on one side of the plane of symmetry on the capsule surface is reproduced identically on the opposite side of the plane of symmetry on the capsule. The smallest measurable size to which mirror symmetry can be applied is 0.15 mm preferably 0.1 mm, more preferably 0.05 mm. If for example the surface of the capsule has projecting points, a pair of (2) projections will also be deemed mirror symmetrical if one projection has a diameter of 1 mm and the other (mirror symmetrical) has a diameter of 0.85 mm. In this case the inaccuracy for the purposes of the present invention is 0.15 mm, etc.

The inaccuracies also include, for example, differences between the capsules on both sides of the plane of symmetry as the result of cone angles of up to 5°, preferably up to 2°, most preferably up to 1°, such as are normally used in order to release the capsules from the tools.

The term "tolerance" should be regarded as a statement of location. The tolerances are preferably 0 to 0.15 mm, preferably 0 to 0.1 mm, more preferably 0 to 0.05 mm. As an example of the term "tolerance", a capsule having a pair of two randomly fixed mirror symmetrical projections in this sense will be acceptable. If one projection is at 0° of longitude (analogously to measurements of the earth) its mirror symmetrical pendant on the other side of the plane of symmetry may be up to 0.15 mm to one side of the degree of longitude in order to be regarded as mirror symmetrical. In this case the tolerance is 0.15 mm.

Thus, two features forming a symmetrical pair on the surface of the capsule may have a tolerance and inaccuracy, deviating from symmetry, of 0.15 mm in each case, preferably 0.1 mm, more preferably 0.05 mm.

Another zone of tolerance and inaccuracy may be allowed above and below the plane of symmetry. This zone above and below the plane of symmetry may have a width of up to 2.5 mm, preferably up to 1.25 mm. It may contain elements, devices, etc. which have no mirror symmetrical pendant or no mirror symmetrically identical pendant on the opposite side of the plane of symmetry. In other words this is a zone of up to 5 mm (2.5 mm above and 2.5 mm below the plane of symmetry) which is excluded from the mirror symmetry. The background to this is that in this zone, in the case of two-part capsules, the join between the two capsule sections is preferably located here, e.g. a weld seam, which naturally cannot be produced in strictly mirror symmetrical fashion. To this extent the join or the seam between the individual elements of the capsule can also be excluded from the mirror symmetry in the narrowest sense with the tolerances specified above.

Also excluded from the mirror symmetry is any possible fine structure of the seam, e.g. the fine structure of a weld seam. Such a seam should be regarded approximately as a line, the height of which corresponds to the height of the weld seam.

Preferably, any elements formed on the capsule surface which are less than 0.1 mm in size, preferably less than 50 microns in size and most preferably less than 10 microns in size are excluded from the mirror symmetry.

The capsule consists of at least two partial elements fitting telescopically one into the other. In a preferred embodiment there are precisely two partial elements, each of these capsule parts having a cavity with three closed sides and one open side. The two partial elements are joined together at their open sides. Preferably this opening is located perpendicularly to the longitudinal axis. In this case the two partial elements are a capsule body and a capsule cap. Preferably the capsules are cylindrical in shape.

The partial elements may be joined together by suitable joining methods after the filling operation. Suitable joining methods include adhesive bonding, banding, shrinking, friction, laser or ultrasound welding.

Alternatively or in addition, the partial elements may also be joined together by clip or snap-in means. In such an embodiment one or more engaging means are provided on the inner surface of the partial element, which is pushed over one of the other partial elements, and complementary engaging means are provided on the outer casing of the other, complementary partial element, which are arranged so that they engage with one another when the capsule is closed. Engaging means of this kind may be similar to projections and recesses operating by he press-stud principle, arranged at points and/or in an annular arrangement around the periphery. Arrangements in which the projections or depressions are disposed in a circle or spiral around the casing are preferred. In one embodiment, one or more projections arranged in an annular arrangement around the inner surface of the cap and the outer surface of the body are designed so that when the capsule is closed a projection of one partial element is located in a depression in the other partial element.

In the embodiments with rings of depressions and/or projections as described above these may be continuous or interrupted.

Preferably, the projections and/or depressions are designed so that they are not visible on the outside.

According to the invention, capsules consisting of two partial elements are preferred. In such cases the seam may be formed parallel to the longitudinal axis or perpendicular thereto. Embodiments with a seam extending perpendicularly to the longitudinal axis are preferred. In this case the seam between the partial elements may bisect the longitudinal axis or may be formed at a point remote from the centre.

In the case of two partial elements the seam is preferably central with respect to the longitudinal axis or offset from the centre by 0 to 12% of the external length, preferably 0 to 10% of the external length away from the centre, more preferably 0 to 5% of the external length away from the centre. In one of the most preferred embodiments the seam is central or is offset from the centre by at most 3% of the external length. Most preferably the seam is in the plane of symmetry.

In the case of two partial elements pushed one into the other along the longitudinal axis the seam may be sealed by any desired sealing method such as adhesive bonding, banding, shrinkage, friction, laser or ultrasound welding.

In embodiments in which the seam is not located centrally, it may be closed off so that the outer casing is smooth at this point and the sealing process does not affect the mirror symmetry of the capsule. In other respects the conditions regarding mirror symmetry and tolerances or inaccuracies are applicable.

The closed capsules according to the invention may have elevations on their outer casing. These elevations may act as spacers when the capsule is placed in the capsule chamber of the inhaler.

The height of the elevations (i.e. the spacing between the base and the apex) is preferably from 0.1 mm to 5 mm, more preferably from 0.5 mm to 2 mm.

The elevations may be in the form of e.g. ribs with sharp edges, with soft undulating transitions or in the form of pins. Combinations thereof are also possible.

The tips or edges of these raised elements preferably have a minimal surface area.

In the case of ribs, these may be arranged axially (=vertically), i.e. parallel to the longitudinal axis of the capsule in the chamber, horizontally or perpendicularly to the longitudinal axis of the capsule or askew with respect to the longitudinal axis of the capsule. The term "askew" also includes helically arranged ribs.

If the ribs are arranged axially, the capsule chamber expediently has at least three or more such ribs. Preferably it has no more than nine, most preferably not more than six ribs of this kind. The length of the ribs is selected so that they guide the capsule as it moves axially without blocking this movement. Preferably, the ribs extend over the full height of the chamber. In this case the ribs preferably have a triangular cross section, one point of the triangle pointing away from the inner surface of the capsule chamber. This embodiment has the advantage that the capsule can be guided in the capsule chamber without any great frictional losses during its axial movement. Other geometric shapes for the ribs are also possible, e.g. ribs with a semicircular or rectangular cross section, etc.

To prevent the capsule from becoming jammed in the axially arranged ribs, it may be advantageous if the spacing between two adjacent pairs of ribs is different (non-equidistant arrangement of the ribs). In this case, the arrangement appears asymmetrical in cross section.

If the ribs are arranged horizontally (=perpendicular to the longitudinal axis) at least two ribs are preferred. They preferably have soft transitions in cross section, i.e. this is a corrugated surface. However, they may also be angular in construction, etc.

A further embodiment of the capsule comprises an outer surface with an undulating pattern as described above, with ribs formed axially on this surface, i.e. perpendicularly to the undulations. These ribs are in turn designed so that the outer edges of the ribs are equidistant to the central longitudinal axis of the capsule chamber and therefore the outer edges of the ribs do not have an undulating surface but a surface which is not curved (parallel to the longitudinal axis).

In the case of pin-shaped elevations these may either be arranged in linear manner and optionally replace the ribs or they may be randomly arranged. The pins will in any case be aligned so that the axial movement of the capsule cannot be disrupted but on the contrary the capsule is guided in its movement.

In all these embodiments, however, the elevations are formed mirror-symmetrically on the outer surface of the capsule, based on the plane of symmetry as defined above.

A preferred capsule, however, has a macroscopically smooth outer surface, i.e. there are no elevations. By the term "macroscopically smooth" are meant surfaces which have elevations and depressions of at most 0.5 mm, preferably up to 0.1 mm, more preferably up to 0.05 mm.

The capsule according to the invention may be circular, oval or n-sided in cross section, where n=3, 4, 5, 6, 7, 8, 9, 10 or more. Preferably the cross section is round or oval.

Preferably, it is a two-part capsule fitting telescopically together, comprising a capsule cap and a capsule body which when closed form a cylinder with tapering ends, preferably hemispherical ends. The cylinder has a longitudinal axis and a transverse axis. The longitudinal axis is the axis which runs parallel to the generatrix of the cylinder casing. The longitudinal axis is longer than the transverse axis with the result that the longitudinal section of the capsule has an oval geometry and the cross section has a circular geometry.

Preferably, a cylinder of this kind has a constant outer cross section starting from the centre until it steadily decreases to form the rounded-off ends.

A cylinder of this kind has a casing which is not curved parallel to the longitudinal axis.

The cylinder may also have a casing which is curved outwardly in concave manner, i.e. away from the central axis (=longitudinal axis). A concave casing of this kind is formed, for example, when the outer diameter of each of the two capsule parts becomes steadily larger, viewed from the tapered end.

In an alternative, less preferred embodiment the outer contour of the casing curves in concave manner.

Finally, the outer casing of each of the two capsule parts may also extend from the tapering end as a straight line initially, running parallel to the longitudinal axis before curving slightly away from the central axis, to run straight again, but then lying at an angle alpha to the central axis until finally it reaches the open end of the capsule part. In this case the outer contour of the capsule fitted together resembles the convex outer contour described above.

The capsule body—or the capsule cap, as desired—may have an edge running round parallel to the inner casing on the inside of its open end, which projects over the edge of the outer casing and can be pushed into the capsule cap and thus connects the two elements (capsule cap and capsule body) to each other. In this way, an encircling edge is formed, parallel to the opening, on the inside of the casing, onto which the capsule cap is then fitted. In other words, the inner casing of this capsule comes higher up than the outer casing, so that a step is formed at the closure point between the capsule cap and the capsule body, on which the other part of the capsule rests in the closed position.

This cylindrical embodiment of the capsule with a macroscopically smooth outer surface and circular cross section may be assigned to symmetry group $D_{\infty h}$ in terms of the symmetrical properties of the outer surface, under idealised conditions. This means that any deviations produced by the manufacturing process can be disregarded and the definitions regarding tolerances and inaccuracies provided above also apply here. This symmetry group includes bodies with a vertical twofold rotation axis (=longitudinal axis), an infinite number of twofold rotation axes standing perpendicular thereto and a plan of symmetry perpendicular to the longitudinal axis, i.e. horizontal. According to the invention, capsules the outer contour of which can be assigned to this symmetry group under idealised conditions as defined above are preferred.

The total length of the closed capsule is preferably 26.1±0.3 mm; 23.3±0.3 mm; 24.2±0.3 mm; 21.7±0.3 mm; 19.4±0.3 mm; 18.0±0.3 mm; 15.9±0.3 mm; 14.3±0.3 mm; 11.1±0.3 mm.

The outer diameter of the capsule body and the capsule cap in the part of the closed capsule which is visible from outside is preferably: 9.91 mm; 8.53 mm; 7.66 mm; 7.64 mm; 6.91 mm; 6.35 mm; 5.83 mm; 5.32 mm; 4.91 mm. The dimensions of the capsule according to the invention are similar to those of size 3 standard commercial capsules, which is known at least in Germany. In the telescopic capsules described the external diameter is preferably between 5.57 mm and 5.83 mm.

Preferably, the capsules should be used in powder inhalers as described for example in the section on prior art above. Specific mention is made of the inhalers according to DE 3345722, WO 91/02558 or EP 0911047. These inhalers are inhalers operating by the Bernoulli principle (Bernoulli inhalers). These inhalers have a capsule chamber the cross section of which is 1.1 to 2.5 times the capsule diameter and the length of which is 1.02 to 2 times the length of the capsule.

The capsule chamber has two openings, an inlet for incoming air and an air outlet. The air inlet is smaller in cross section than the capsule chamber so that in this region of the capsule chamber a relatively high flow velocity is obtained which intensifies the Bernoulli effect by which the powder in the capsule is finally delivered. The air inlet opening is conveniently arranged centrally in the base of the chamber. On the air outlet side there may be a perforated plate or other device such as projecting components to prevent a capsule moving in the capsule chamber from sliding into the air outlet and thus blocking it or any capsule fragments formed from being sucked into the mouthpiece. The perforated plate may for example be part of a funnel-shaped connecting member which can be fitted on to the start of the inhalation channel leading to the mouthpiece in such a way that the edge of the funnel with the perforated plate engages in a plate-shaped insert which forms the base of the mouthpiece. The perforated plate may, however, also be replaceably fixed by jamming it between the funnel edge of the connecting member and a stop of the plate-shaped insert.

A plurality of openings may also be provided as the outlet opening. The cross section available for the air to flow out of the capsule chamber is conveniently greater at every point than the air inlet opening so that the air charged with the pharmaceutical composition can flow out unimpeded as far as possible. The air outlet opening is expediently arranged centrally in the top of the chamber but may also be arranged to one side in the top region.

The provision of the two openings is intended to guide an air stream axially through the capsule chamber.

The capsule chamber has at at least one point along its longitudinal axis (in relation to the interior of the capsule chamber) an opening for or a connection to a cutting device which is provided with at least two sharp spikes or cutters for piercing or cutting open a capsule located in the capsule chamber. The cutting device is moveable into the interior of the chamber counter to the pressure of the spring and is operated by means of a spring mounted actuating button. As the height of the capsule chamber is determined by the length of the pharmaceutical capsules, the points or cutters of the cutting device are preferably located close to the top or bottom end of the capsule chamber. The side wall of the capsule chamber may have radial bores or oblong slots in the region of its top and bottom end which face the spikes or cutting edges and serve to allow the spikes or cutters to pass through. The dimensions of these bores/slots are matched to the cross section of the spikes or cutting edges.

In a preferred embodiment the guide for the spikes of the cutting device comprises a sealing plate. In this way the seal between the capsule chamber in the inhaling position and the cutting device is improved. For the spring mounting of the sealing plate it is possible to use the spring which resets the actuating button for the cutting device.

Finally, in another embodiment, a lever system is provided for actuating the cutting device. This lever system is preferably actuated by an actuating button mounted on the base or side of the housing of the inhaler. The lever system may consist of a rocker and a toggle lever, while the actuating button acts on one end of the rocker and the other end of the rocker presses on one end of the toggle lever, the other end of the toggle lever secured to the cutting device pushing the cutting device forward. The rocker and toggle lever are preferably mounted to be pivotable about axes in holders secured to the housing.

The capsule is supposed to be opened close to both its ends for the inhalation process. The hemispherical caps of the capsule should not be damaged thereby. This is important because the capsule or cap of the capsule acts as a sort of valve. Because of the pressure conditions the capsule is pulled towards the inlet opening counter to the inflowing air and closes it off. As the user continues to suck on the mouthpiece, suction is produced in the capsule chamber by which the capsule is pulled towards the air outlet with the inflowing air. The suction now formed at the air inlet ensures that the capsule is pulled towards the inlet opening again. The entire process is repeated in rapid succession as long as the patient continues to inhale through the mouthpiece and sets the capsule vibrating strongly in the axial direction.

The powder inhalers fitted with a capsule according to the invention, which in the simplest case consists of a capsule chamber, an air inlet opening, an air outlet opening connected to a mouthpiece and a device for piercing the capsules, are also an object of the present invention.

The air mixed with the pharmaceutical composition in the chamber in the form of a powder aerosol is passed through the mouthpiece to the user's mouth. The mouthpiece which is generally tubular and optionally somewhat flattened may be arranged axially or at an angle to the axis of the chamber or laterally with respect to the axis of the chamber.

The mouthpiece of the inhaler may be constructed in the form of a cap which is fitted on to a lower part of the inhaler which contains the capsule chamber. This cap may be hinged to the edge of the inhaler housing so as to be pivotable about an axis extending perpendicularly to the longitudinal axis of the inhaler. The mouthpiece and the lower part of the inhaler housing may, however, also be fixed to one another by a conventional push-fit connection. In any case, access generally, to the capsule chamber and to the cutting device in the lower housing part, on the one hand, and to the inner components such as the perforated plate and the upper housing part (of the mouthpiece-like cap) is made substantially easier by the removability or pivotability of the two components.

In order to replace used capsules with fresh ones, in an embodiment of this kind the mouthpiece is flipped upwards or the push-fit connection between the mouthpiece and the lower housing part is undone. The capsule chamber is then freely accessible, so that the emptied capsule can be removed and a full one inserted. The device is then flipped shut or pushed shut.

The inhaler according to the invention makes it possible to deliver the pharmaceutical composition more reliably than with devices known from the prior art, with lower standard deviations, and ensures good cleaning thereof.

Preferred inhalers are those described hereinbefore as embodiments of DE 3345722, WO 91/02558 or EP 0911047. Reference is hereby made once again to the features mentioned in this section. The inhaler as described hereinbefore in connection with EP 0911047 is particularly preferred.

In inhalers of this kind there is only one capsule chamber for accommodating the capsule according to the invention, in accordance with the remarks on DE 3345722 or EP 0911047.

Other inhalers comprise a revolver magazine with a plurality of usually tubular chambers each adapted to be loaded with one capsule. The magazine is covered at each of its two open ends by a plate, one plate containing the air inlet opening and axially thereto the other plate containing the air outlet opening. As the magazine is rotatably mounted within these plates, one of the chambers can be pivoted into place between the two openings and thus form part of the continuous channel for the inhaled air. After an inhalation process has ended the revolver magazine is further rotated until the next chamber enters the air throughflow channel. One of the two plates may be separated from the magazine, for example, in order to remove used capsules from the chambers, or else the entire magazine can be removed for refilling, for example.

According to a further feature of these inhalers the revolver magazine is releasably mounted in the inhaler housing. After the capsules in the revolver magazine have been used the entire revolver magazine can be replaced or refilled with capsules.

The inhaler housing may have an eccentrically mounted pin on to which the revolver magazine can be fitted.

In order to fix the position of the revolver magazine it may be provided with recesses associated with the capsule chambers for a spring-mounted locking bolt arranged in the inhaler housing. The recesses are arranged so that the locking bolt only engages therein when one of the capsule chambers is located precisely between the air inlet and outlet.

In this way it is possible to ensure that the revolver magazine does not move during the inhalation. The spring mounting of the locking bolt should be selected with regard to the spring constant so that accidental rotation of the revolver magazine is prevented by the locking but on the other hand if greater force is applied the revolver magazine can be rotated out of its locked position. Conical shapes for the free end of the locking bolt and suitably shaped recesses have a supporting effect.

The locking bolt is preferably arranged coaxially with the air throughflow channel underneath the capsule chamber and has a through-bore which simultaneously forms the air inlet in the base. Preferably, the locking bolt is centrally mounted in the inhaler housing. According to another embodiment of the invention the locking bolt is acted upon by a spring the other end of which abuts on a stopper releasably fixed in the inhaler housing, which also has a central through-bore which is part of the air throughflow channel.

In a preferred embodiment the recesses for engagement of the locking bolt in the base are arranged in the base plate of the magazine, concentrically with the air inlet bores of the capsule chambers and constructed like the casing of a flat truncated cone with its base facing outwards. Thus, these recesses are conical or funnel-shaped widenings of the air inlet bores, the widened area facing the locking bolt. The slopes produced by the widening correspond approximately to the chamfers on the top of the locking bolt.

In a preferred embodiment these recesses have an encircling stop edge on the base of the casing of the truncated cone, but also in the base plate, which acts as a rotation preventer or stop for the head of the locking bolt when the latter has engaged in the corresponding recess. Because of this stop edge the magazine cannot be turned any further once the locking bolt has engaged.

According to another feature of this embodiment the said stop edge takes up only part or half of the periphery of the conical recess, i.e. the funnel-shaped widening, and is arranged so that when the locking bolt is engaged it prevents rotation of the magazine in one direction but allows it in the other direction, as the sloping wall of the funnel-shaped widening merges smoothly into the exterior of the base plate.

In another preferred embodiment only one of the recesses has a stop edge which takes up the entire circumference of the recess so that when the locking pin is engaged it is impossible for the magazine to rotate in this recess. This position is then regarded as the end position of a magazine in which all the capsules have been used. In this embodiment, all the other recesses only have a rotation preventer on one side, i.e. effective in one direction, so that the magazine can only ever be rotated in the direction in which a capsule chamber containing an unused capsule is brought into play, until the end position described above in which locking is complete is reached. The user then knows that the magazine has to be loaded with fresh capsules once this last capsule has been used.

In another preferred embodiment a tongue may be fixed to the locking bolt which extends as far as a stop on the inside of the operating button of the cutting device when the locking bolt assumes its upper stop position with the revolver magazine removed. In this position the said tongue acts as a barrier for the cutting device. When the magazine is inserted the locking bolt is pressed down again and in this way the barrier for the cutting device is removed.

The actuation of the cutting device may also be coupled to the rotary movement of the capsule magazine, so that at the press of a button first a capsule chamber is brought into the correct position and then the cutting device is engaged.

If the revolver magazine and the part of the inhaler housing adjacent thereto are constructed with n angles, where n is a whole number indicating the number of capsule chambers, the side surfaces of the inhaler housing part and of the revolver magazine may advantageously be aligned when the magazine is in the correct position. It is then possible to determine immediately from outside whether the chamber is located in the air channel defined by the air inlet and the air outlet.

BRIEF DESCRIPTION OF THE DRAWINGS

The invention will now be explained more fully with reference to the Figures.

FIGS. 5 to 15a and 15b show different embodiments of the capsule according to the invention.

DETAILED DESCRIPTION OF THE INVENTION

Figure 1:
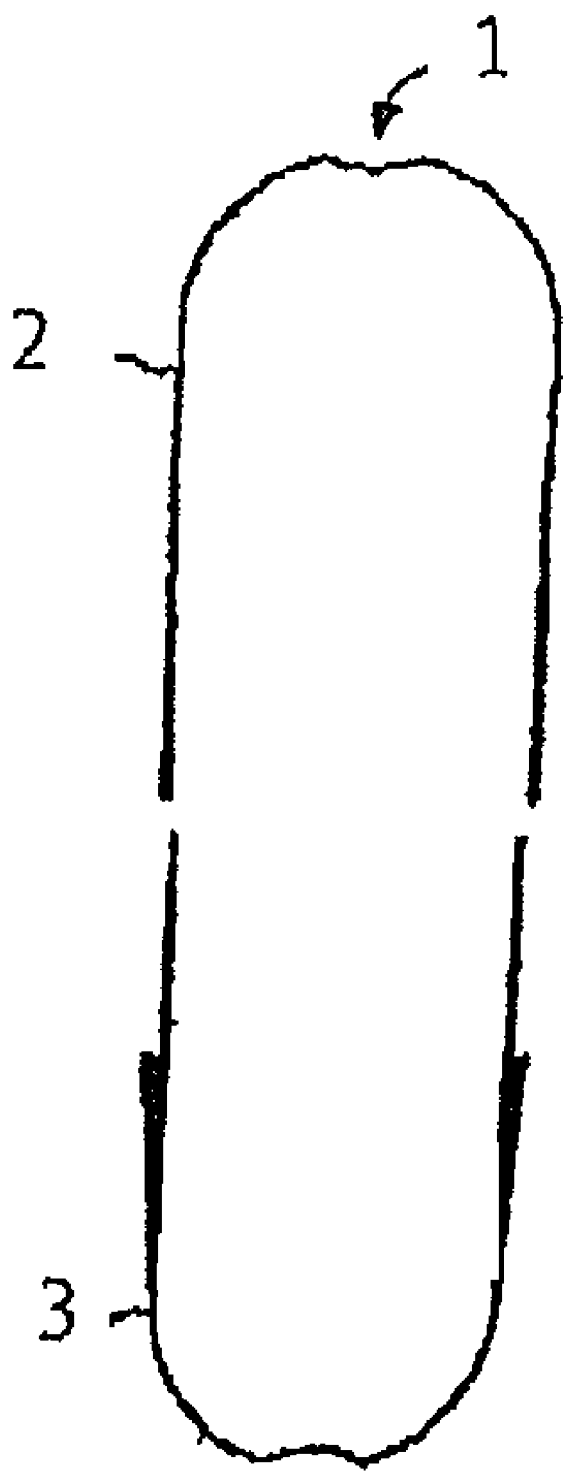
FIG. 1 shows a closed capsule known from the prior art.

FIG. 1 shows a capsule (1) known from the prior art, consisting of a capsule cap (2) and a capsule body (3). It can be seen that the outer diameter of the capsule body is smaller than that of the capsule cap over wide areas. This is particularly noticeable in the region of the hemispherical bottom end of the capsule body.

Figure 2:
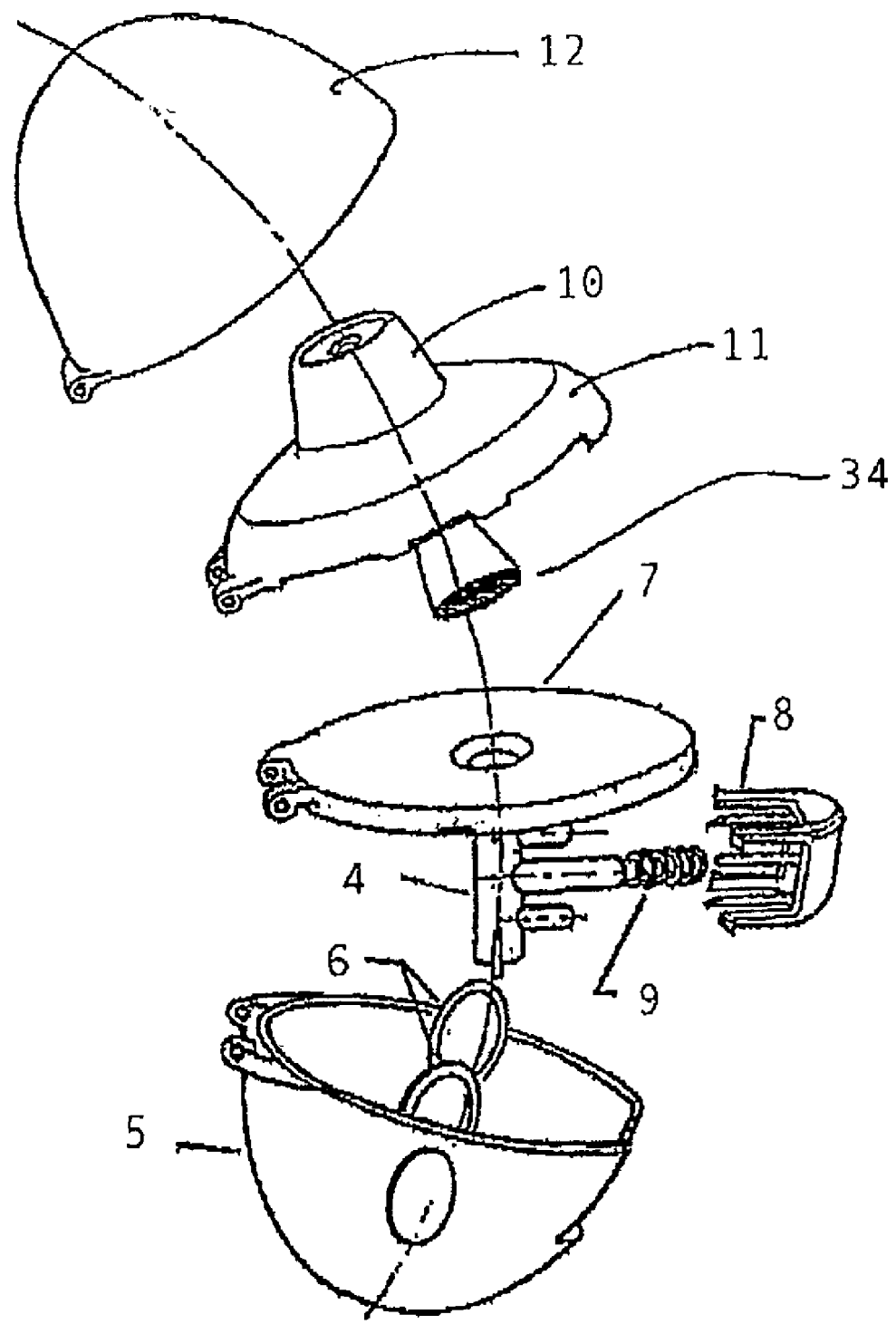
FIG. 2 shows an inhaler in which the capsule according to the invention can be used.

FIG. 2 shows how an inhaler may be constructed in which a capsule chamber according to the invention is integrated. Located in a lower part (5) optionally with two windows (6) is a plate (7) connected to the capsule chamber (4). The capsules in the capsule chamber (4) are opened by means of a button (8) provided with two specially sharpened spikes which is pressed in counter to the pressure of the spring (9) and thereby cuts open or pierces the capsule in the chamber in two places. As the user inhales through the device using the mouthpiece (10) which is connected to the upper part (11), the air enters the lower part (5) and from there goes into the capsule chamber (4) at the lower end. The device is closed off by a lid (12), which is hinged to the lower part (5), the plate (7) and the upper part (11), so that when the lid is closed dust cannot enter the device. In the plate (7) there may optionally be capsule holders in the form of blind bores. Advantageously, there is a perforated plate (34), which is fixed to the lower end of the mouth tube (10) or of the inhalation channel leading to the opening of the mouthpiece and, when the inhaler is in the closed position, covers the air outlet opening of the capsule chamber (4). The drawings do not show optional snap-fit hooks on the side of the mouth tube (10) or of the upper part (11) which is oriented towards the plate (7), which are capable of engaging in the plate (7). In this case the plate (7) has suitably complementary devices (depressions or holes). Projections or snap fit hooks may also be provided laterally on the plate (7), for example, to enable the plate (7) to engage in the lower part (5). The above mentioned devices for engaging the mouthpiece (10) or upper part (11) in the plate (7) or the plate (7) in the lower part (5) are such that the individual elements can easily be separated from one another again. In addition, a lug may be formed on the point on the lid (12) which is located above the button (8) in the closed position so that this lug engages in a depression on the top of the button (8) and blocks the button (8), so that the button (8) cannot be pressed in the closed position. This prevents the capsule from being accidentally perforated prematurely once it has been inserted in the capsule chamber.

Figure 3:
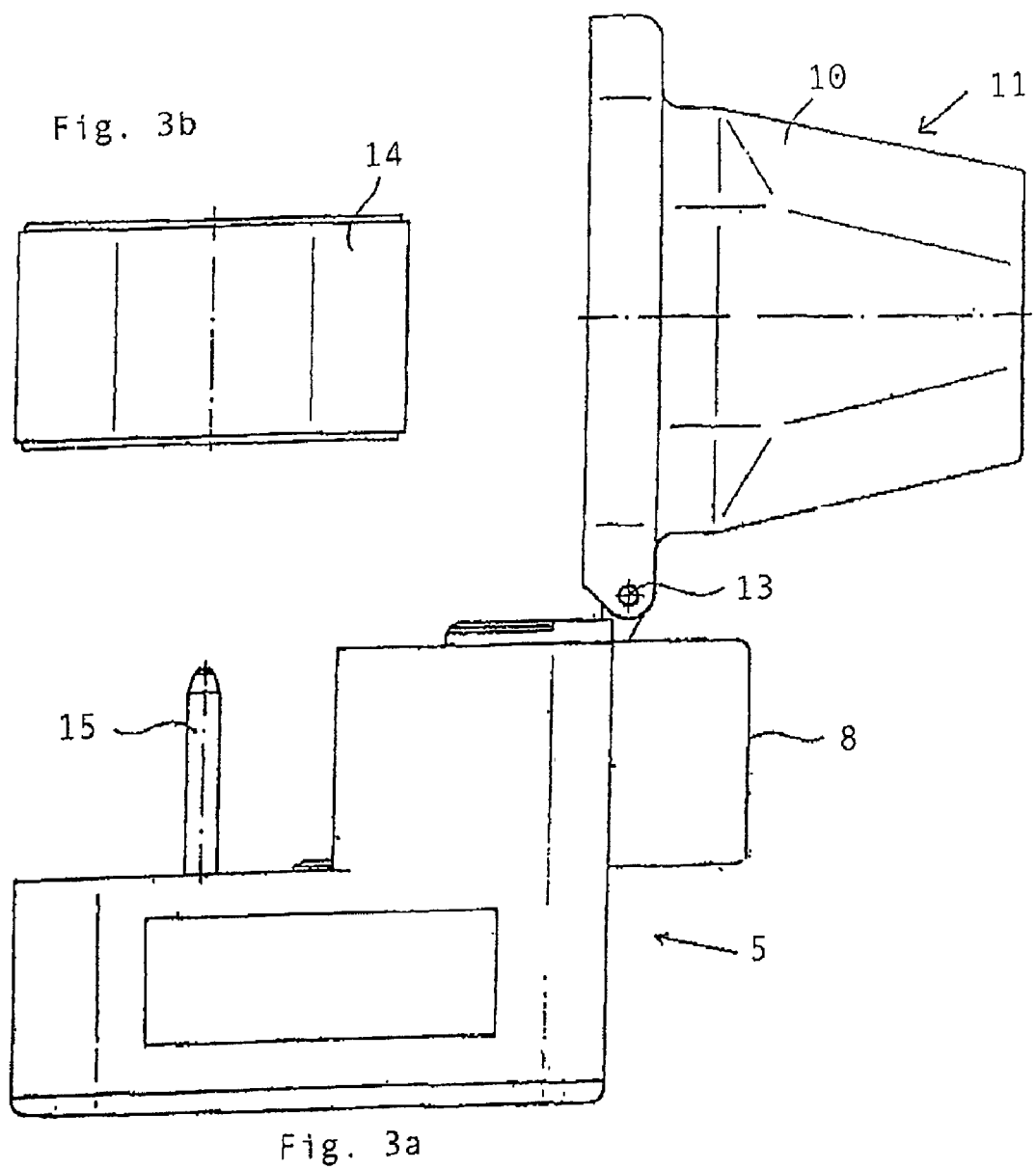
FIGS. 3a to 3d show a powder inhaler with a revolver magazine in which the capsule according to the invention can be used.
Figure 3C:
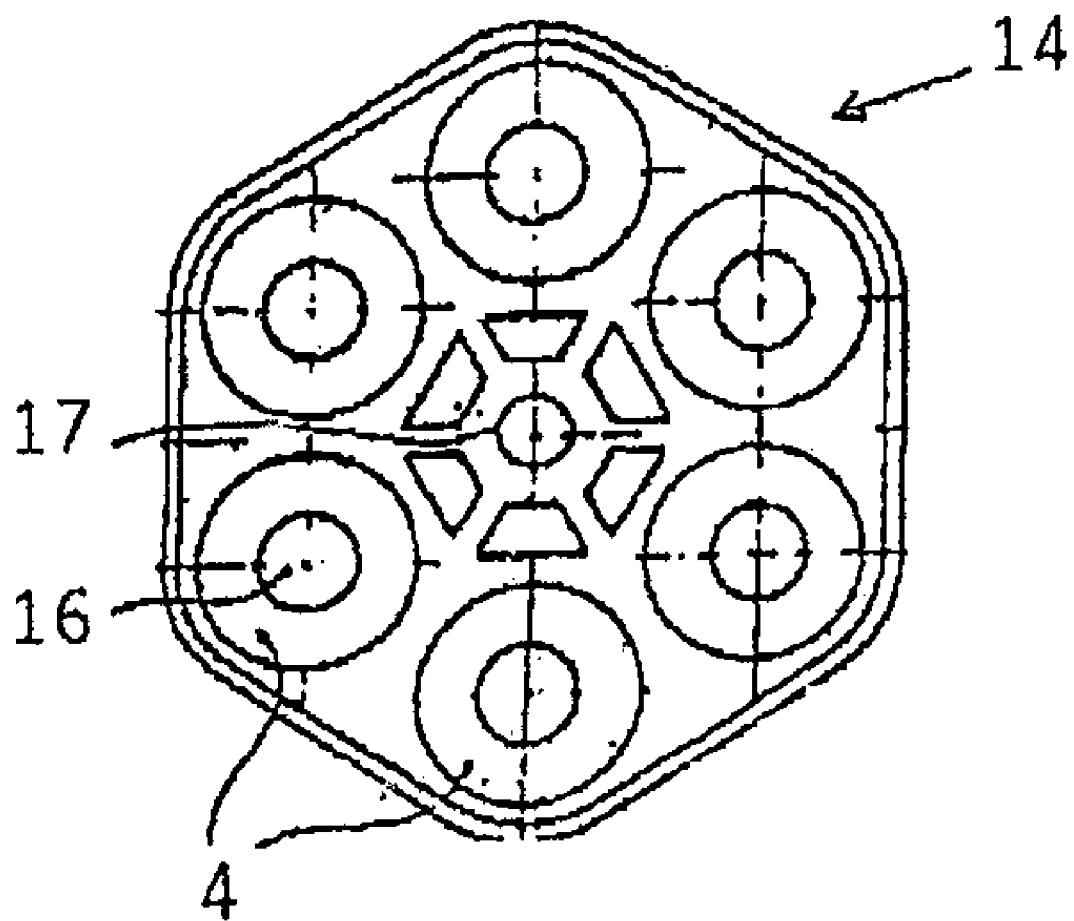

FIG. 3: As can be seen from FIGS. 3a, 3b and 3c, an inhaler with a revolver magazine consists essentially of an inhaler housing (5) with a mouthpiece (10) which is hinged laterally to the upper edge of the inhaler housing (11) so as to be pivotable about an axis (13), and a revolver magazine (14) with the capsule chambers (4) for accommodating the capsules. The revolver magazine (14) can be fitted on to a pin (15) eccentrically mounted in the inhaler housing (5).

After the revolver magazine (14) has been pushed on the mouthpiece (10) is moved into its normal position—as a cap on the housing; the inhaler is ready for use. A capsule (not shown) can now be perforated by pressing the button (8). As can be seen from FIG. 3c, the revolver magazine (14) in this case has 6 chambers (4) for accommodating the capsules (not shown). The base of each chamber (4) has an air inlet bore (16). In addition, the revolver magazine (14) has an axial guide (17) for the pin (15).

Figure 3D:
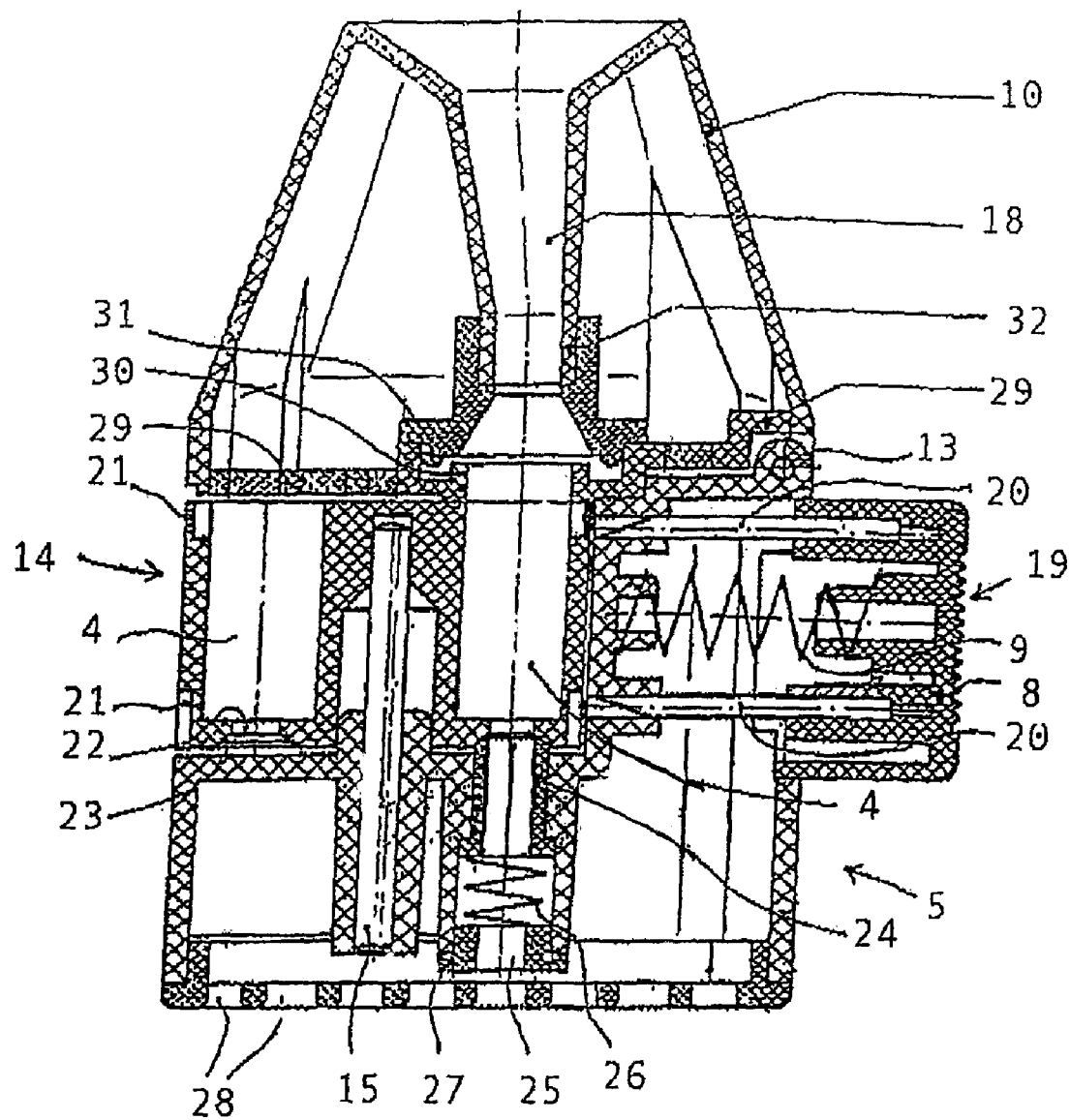

As may be seen from FIG. 3d, the inhaler has, adjacent to the chamber (4) mounted underneath the inhalation channel (18), the cutting device (19) which is operated by means of the button (8). This cutting device (19) has two spikes (20) which can be radially inserted into the upper and lower part, respectively, of said chamber (4), the outer wall of the revolver magazine having weakened or frangible regions (21) at suitable points to assist the insertion of the spikes (20). The spikes (20) serve to open the capsule located in the chamber (4) close to the upper and lower ends thereof. The revolver magazine (14) also has, underneath the bores (22), conical recesses (23) in which a locking bolt (24) can engage as soon as the corresponding chamber (4) is coaxial with the air inlet or inhalation channel (18) of the inhaler housing. The locking bolt is also conically formed at its end engaging in the recess (23). At the opposite end it is acted upon by a spring (26) which bears on a stopper (27) releasably fixed in the inhaler housing. This stopper, like the locking bolt, has a central through-bore which acts as an air inlet (25).

In order to prepare the inhaler, with the revolver magazine (14) in place, this magazine is rotated so that one of the chambers (4) is brought into a position in which the bore (22) in the base or the conical recess (23) is aligned coaxially with the air inlet opening (25). The positioning of the chamber (4) is made easier by the engagement of the locking bolt (24) in the recess (23). After the bolt has engaged, the air inlet opening (25) and the base opening (22) in the chamber (4) are in alignment. The cap of the capsule is positioned on the base opening (22) and closes it off. By actuation of the button (8) counter to the force of a spring (9) the cutting edges (20) are moved radially towards the chamber (4), first piercing the weakened regions (21) or entering corresponding openings in the side wall of the revolver magazine and finally opening the capsule at the top and bottom close to its ends. The tapering caps of the capsules should not be destroyed as they are intended to act as a kind of valve.

When air is then sucked through the mouthpiece (10), the air flowing into the chamber (4) from the base openings (28) in the housing (5) and the air inlet (25) sets the capsule vibrating violently, produces turbulence in the powder in the capsule, mixes with it and is finally inhaled. The mouthpiece (10) is generally tubular in construction but may also be adapted to the shape of the mouth and flattened. Similarly, as an alternative to the embodiment shown, the mouthpiece may be arranged axially or at an angle to the axis of the chamber or laterally offset from the axis of the chamber.

At the base, the mouthpiece (10) may be provided with a plate-shaped insert (29) which is essentially solid. This plate-shaped insert (29) may also have perforations, however. Moreover, the start of the inhalation channel (18) may be covered with a screen which prevents the capsule or capsule fragments from being inhaled into the inhalation channel (18) in the mouthpiece. Alternatively, projections may be provided on the wall at this point to hold the capsule back. The perforated plate is then preferably arranged in the centre of the plate-shaped insert (29), advantageously clamped between a stop (30) on the plate (29) surrounding the air throughflow and the edge of a funnel-shaped connecting member (31), which is fitted on to the beginning (32) of the inhalation channel (19) in such a way that the edge of the funnel faces the plate-shaped insert (29) and engages therewith. The alternatively provided projections may also be arranged at this point.

Figure 4:
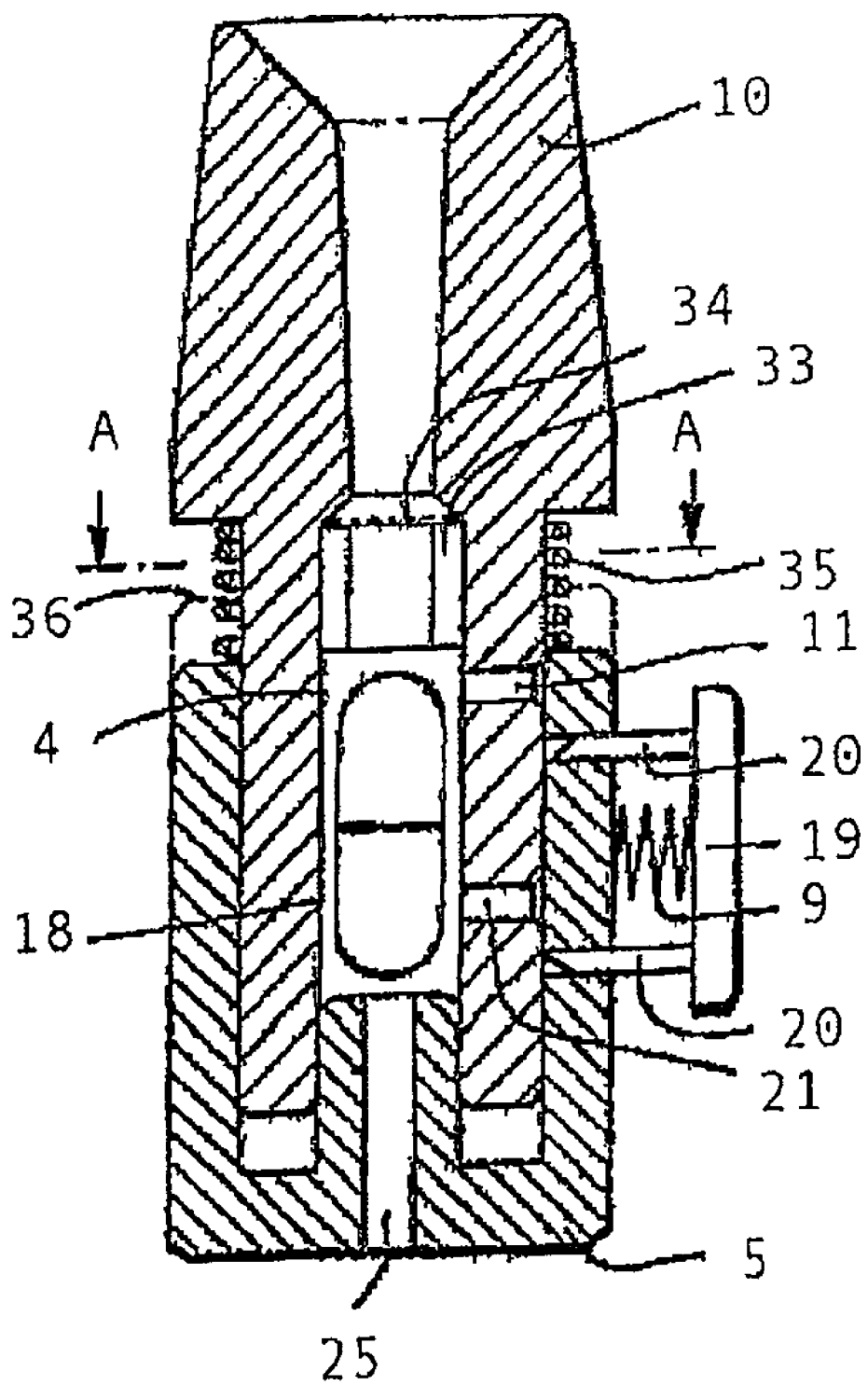
FIG. 4 shows a powder inhaler with an upper part and lower part which are movable relative to one another.

The embodiment of the inhaler according to the invention as shown in FIG. 4 consists of the lower part (5) and the mouthpiece (10), which are fitted together. The lower part contains the air inlet channel (25) which is connected to the air inlet into the capsule chamber (4). The cutting device (19) is held in its normal position by a spring element (9). The mouthpiece (10) contains the capsule chamber (4). Projections (33) which limit the play of the capsule project into the extension of the capsule chamber. A perforated plate (34) prevents fragments of capsule from being inhaled, for example. The inhaler may be axially compressed counter to the pressure of a spring element (35), the upper edge of the lower part reaching the position (36). In this position the blades or points (20) of the cutting device (19) may penetrate through the opening (21) into the capsule chamber (4) and open the capsule secured therein.

In order to use the inhaler according to FIG. 4 the lower part (5) and mouthpiece (10) are pulled apart, the capsule is inserted and the two parts of the inhaler are fitted together. After being pressed back into position (36) counter to the spring element (35) the cutting device (19) is actuated and released again. Under the pressure of the spring element (35) the inhaler returns to the initial position shown in FIG. 4. The active substance formulation from the capsule (not shown) can now be inhaled by breathing in through the mouthpiece (10).

Figure 5:
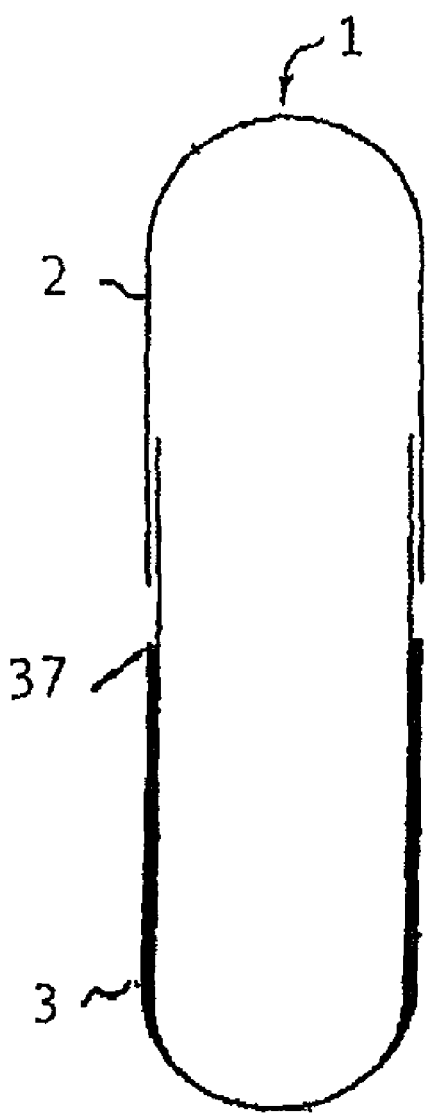
Figure 6:
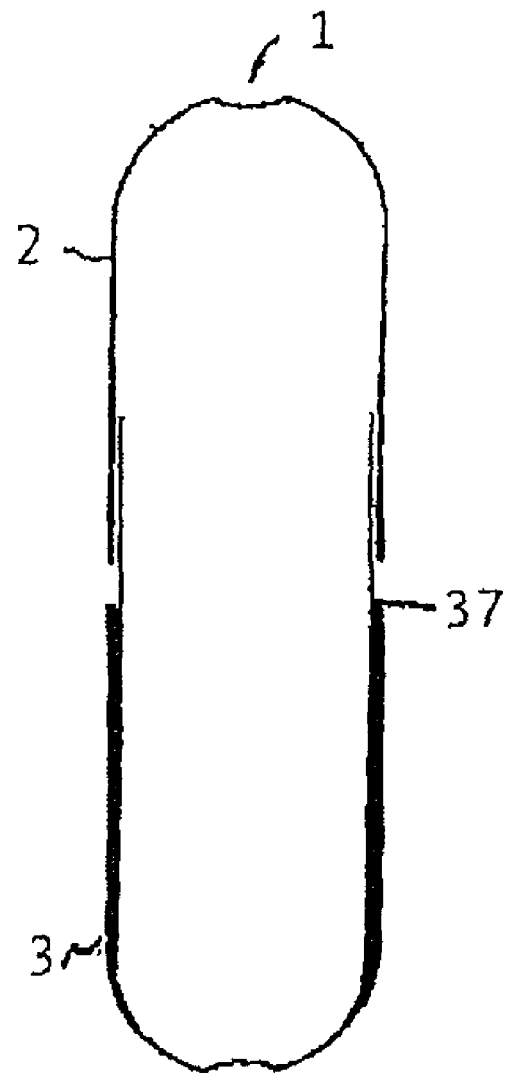

FIGS. 5 and 6 each show a mirror-symmetrical capsule (1) according to the invention consisting of a capsule cap (2) and a capsule body (3). The capsule body has on the inside an inwardly engaging extension (37) which is inserted in the capsule cap. The substantially perfectly hemispherical ends as shown in FIG. 5 are preferred in the case of hard gelatine capsules. In the case of capsules produced by injection moulding the injection points at the ends are somewhat depressed (FIG. 6).

Figure 7A:
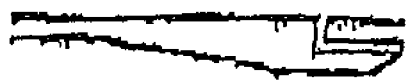
Figure 7B:
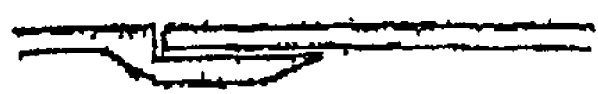
Figure 7C:
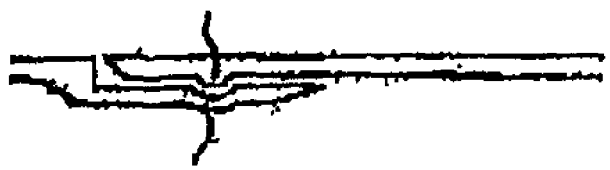

FIGS. 7a to d show different sealing techniques using engaging means on the capsule cap and capsule body. In FIGS. 7a to 7c the smooth side is the outside in each case. In a variant according to FIG. 7d the smooth side may be the inside or the outside of the closed capsule.

FIG. 7c comprises engaging means which resemble press-studs, having a projection (38) on one of the capsule elements and a depression (39) for the engagement of the projection on the other capsule element.

Figure 7D:
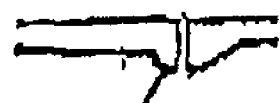

The alternative method of sealing shown in FIG. 7d comprises a projection (40).

FIG. 8 shows a variant in which the side wall of the capsule cap (2) tapers abruptly (41), viewed from the open to the closed end. The capsule body can then only be pushed into the capsule cap until it reaches the tapered part (41) from the inside. The position of the taper is selected so that the mirror symmetry of the closed capsule is maintained.

FIG. 9 shows a variant in which the seam between the capsule cap (2) and the capsule body (3) is not in the plane of symmetry.

Figure 10:
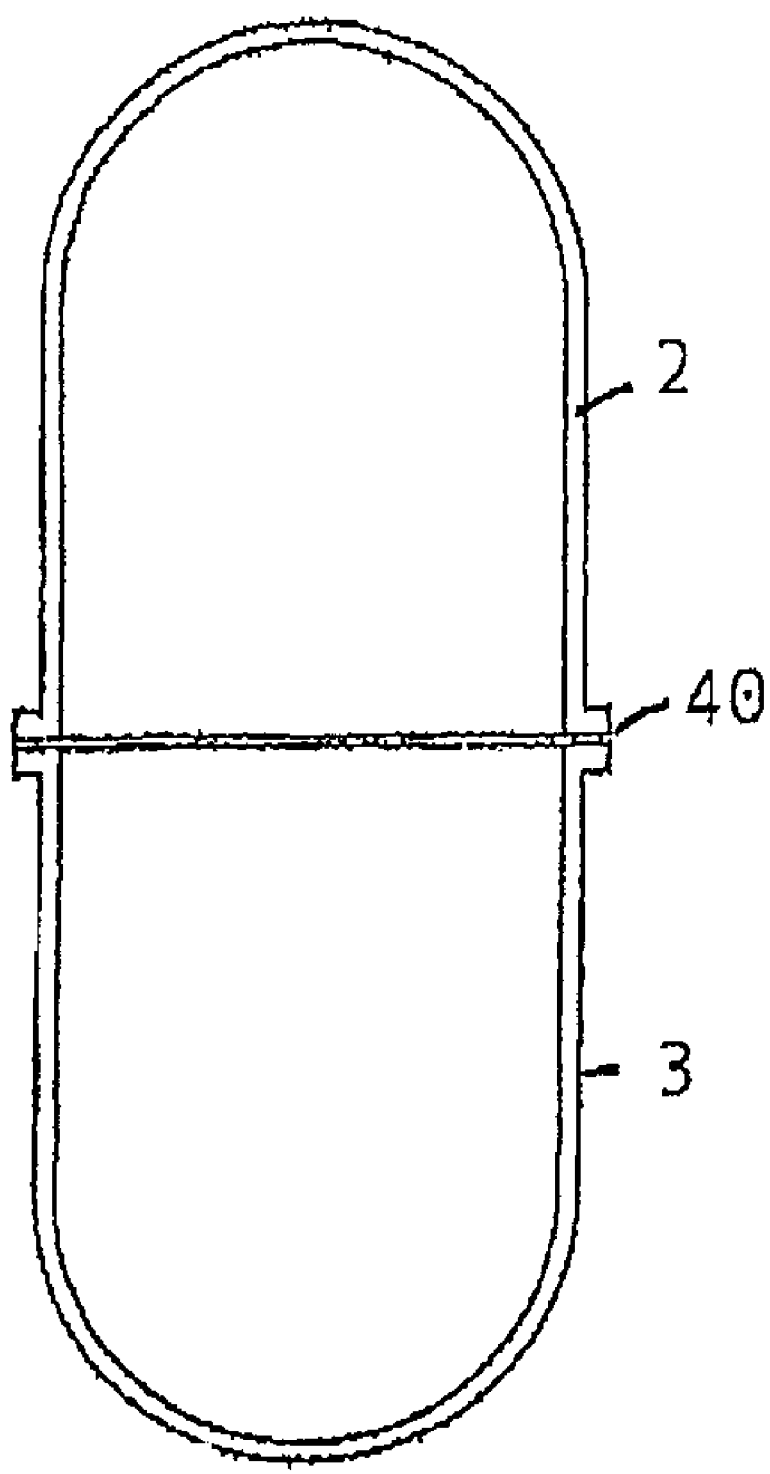

FIG. 10 shows a variant with a closure according to FIG. 7d.

Figure 11:
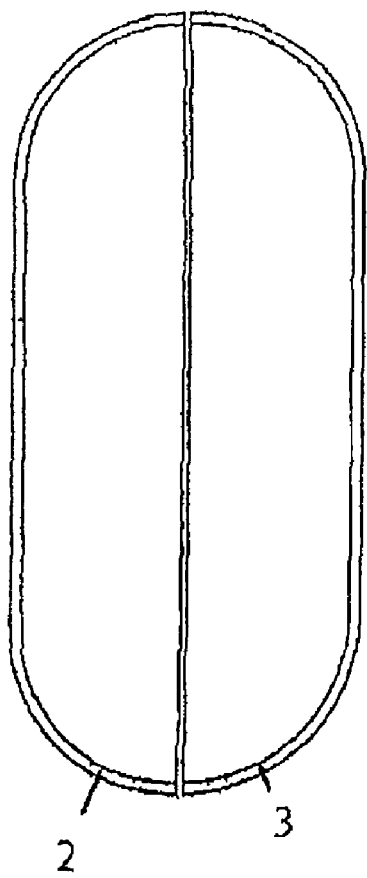

FIG. 11 shows a variant with a seam running parallel to the longitudinal axis.

Figure 12:
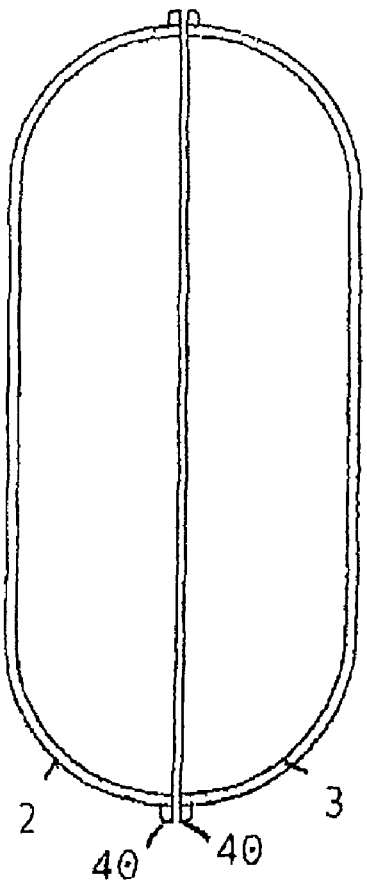

FIG. 12 shows a variant according to FIG. 11 with a closure according to FIG. 7d.

Figure 13:
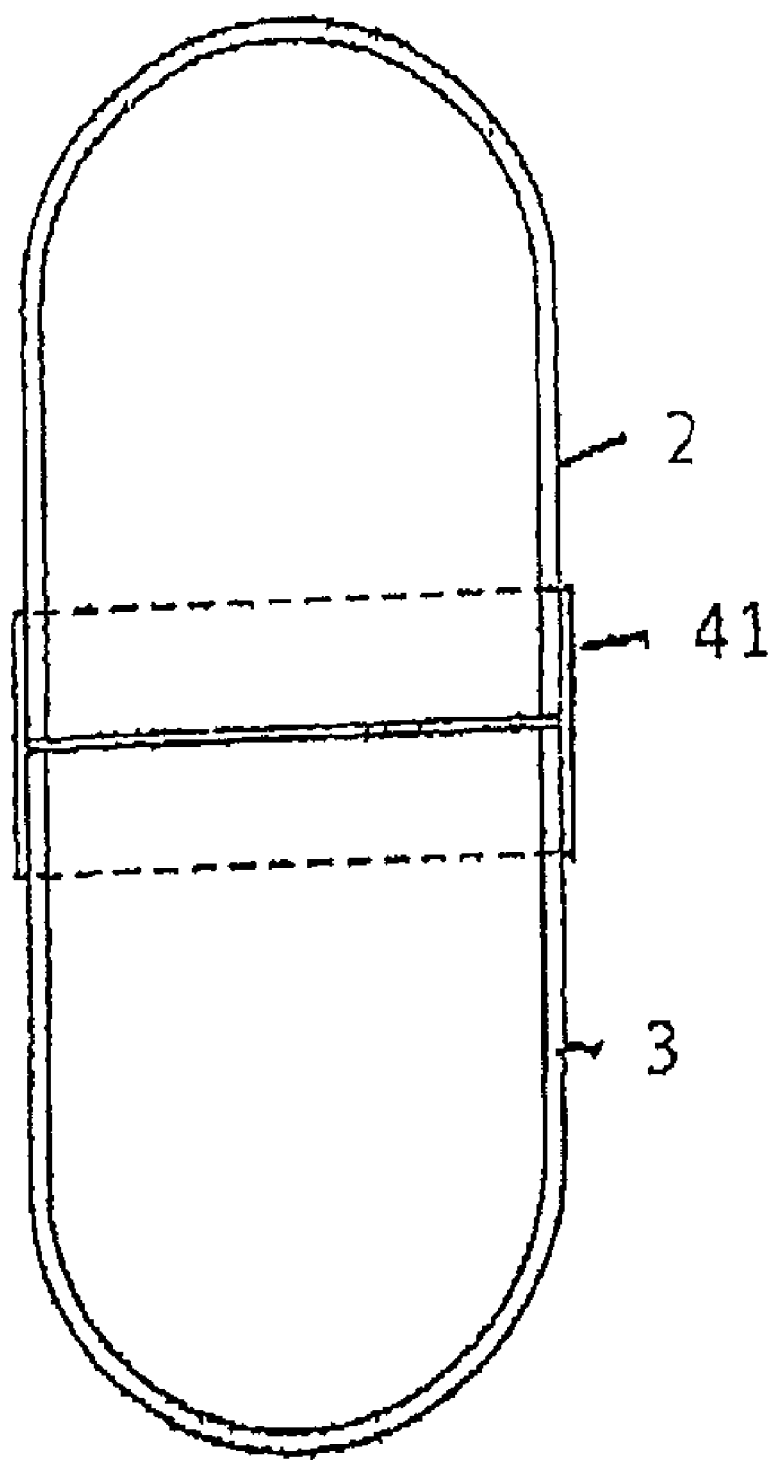

FIG. 13 shows a variant with a seam running perpendicularly to the longitudinal axis, this seam being banded (41).

Figure 14A:
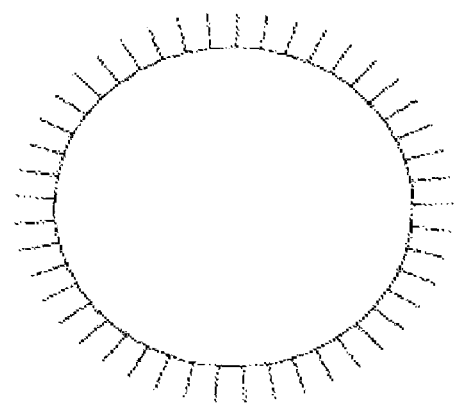

FIG. 14a shows a schematic diagram of a transverse cross sectional view of an inhaler capsule with ribs in the form of pins on the outer contour.

Figure 14B:
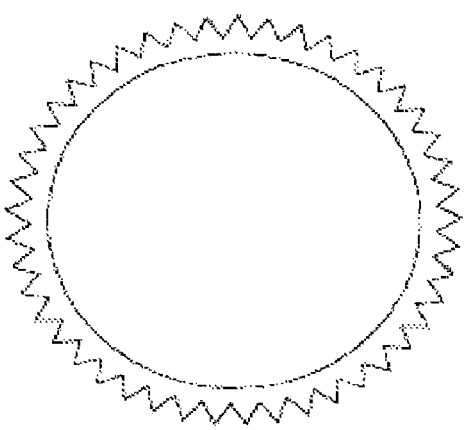

FIG. 14b shows a schematic diagram of a transverse cross sectional view of an inhaler capsule having ribs with sharp edges on the outer casing.

Figure 14C:
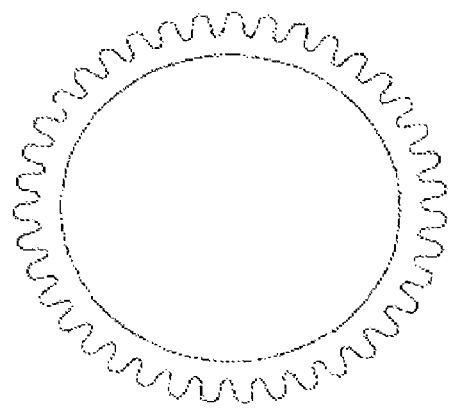

FIG. 14c shows a schematic diagram of a transverse cross sectional view of an inhaler capsule having ribs with soft undulating transitions on the outer contour.

Figure 15A:
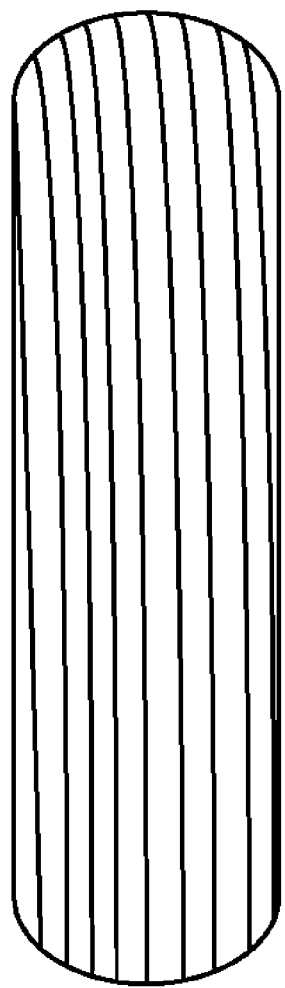

FIG. 15a shows a schematic diagram of a capsule for an inhaler having an outer contour comprising longitudinal ribs or ribs arranged vertically or ribs arranged parallel to the longitudinal axis in accordance with an embodiment disclosed herein.

Figure 15B:
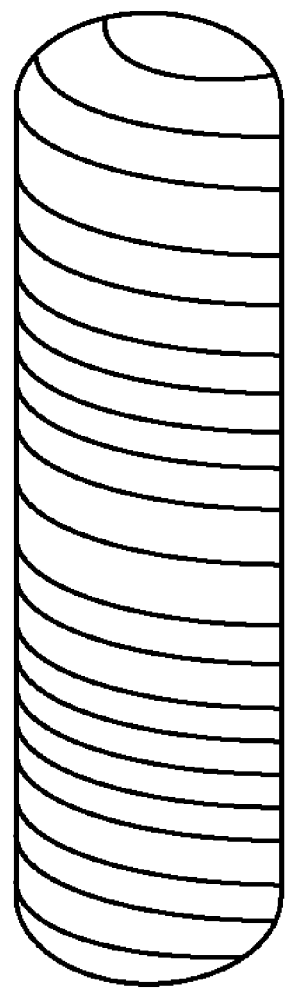

FIG. 15b shows a schematic diagram of a capsule for an inhaler having an outer contour comprising helical ribs in accordance with an embodiment disclosed herein.

The invention claimed is:

1. A capsule for holding a pharmaceutical composition in a Bernoulli inhaler, the capsule comprising:
   two parts in communication with one another such that, in a closed state, the two parts define the longitudinal axis and a transverse axis which is shorter in relation to the longitudinal axis; and
   elevations on an outer surface wherein the elevations are in a form of at least one of longitudinal ribs, and helical ribs,
   wherein features forming an outer contour of the closed capsule are symmetrical with respect to a transverse plane which bisects the longitudinal axis, the following features being excluded from conditions of symmetry: fine structures of any seams comprising sealed seams of individual parts of the capsule, elements formed on a capsule surface which are smaller than 0.1 mm, and/or angles of taper up to 5°.

2. The capsule of claim 1, wherein the two parts are operable to be pushed telescopically one inside the other along the longitudinal axis.

3. The capsule of claim 2, wherein a seam created between the two parts of the closed capsule is offset from the center by 0 to 12% of the outer longitudinal length.

4. The capsule of claim 1, wherein any seam created between the two parts when the capsule is closed is offset from the center by 0 to 12% of the outer longitudinal length.

5. The capsule of claim 1, wherein the capsule has a cylindrical outer contour.

6. The capsule of claim 5, wherein the capsule has tapering sealed ends.

7. The capsule of claim 1, wherein the capsule comprises a member of the $D_{\infty h}$ symmetry group in terms of its outer contour, irrespective of the seam between the two parts of the capsule and irrespective of any manufacturing tolerances.

8. The capsule of claim 1, wherein features located on the outer contour of the capsule surface and forming a symmetrical pair may have a tolerance and inaccuracy deviating from the symmetry of 0.15 mm in each case.

9. The capsule of claim 1, wherein the elevations are in the form of at least one of ribs with sharp edges, ribs with soft undulating transitions, ribs in the form of pins and combinations thereof.

* * * * *